(12) United States Patent
Hacker et al.

(10) Patent No.: US 8,408,703 B2
(45) Date of Patent: Apr. 2, 2013

(54) SPECTROMETER

(75) Inventors: Martin Hacker, Jena (DE); Roland Bergner, Jena (DE); Ralf Ebersbach, Schmoelln (DE); Klaus-Ditmar Voigt, Jena (DE); Roland Barth, Jena (DE); Eberhard Hofmann, Bollberg (DE); Peter Klopfleisch, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 298 days.

(21) Appl. No.: 12/680,574

(22) PCT Filed: Sep. 24, 2008

(86) PCT No.: PCT/EP2008/008096
§ 371 (c)(1),
(2), (4) Date: May 5, 2010

(87) PCT Pub. No.: WO2009/043517
PCT Pub. Date: Apr. 9, 2009

(65) Prior Publication Data
US 2010/0214533 A1    Aug. 26, 2010

(30) Foreign Application Priority Data
Sep. 28, 2007 (DE) .......................... 10 2007 046 504

(51) Int. Cl.
*A61B 3/14* (2006.01)
*A61B 3/00* (2006.01)
(52) U.S. Cl. ......... 351/206; 351/205; 351/246; 382/128
(58) Field of Classification Search .................. 351/206, 351/205, 207, 213, 214, 220, 221, 246, 200; 359/212.1–215.1, 205.1–207.6
See application file for complete search history.

(56) References Cited

U.S. PATENT DOCUMENTS

| | | | |
|---|---|---|---|
| 5,373,359 A | 12/1994 | Woollam et al. | |
| 5,777,733 A | 7/1998 | Radzuik | |
| (Continued) | | | |

FOREIGN PATENT DOCUMENTS

| | | |
|---|---|---|
| WO | WO 2004/043245 | 5/2004 |
| WO | WO 2006/021929 | 3/2006 |
| (Continued) | | |

OTHER PUBLICATIONS

International Preliminary Report on Patentability and Written Opinion for PCT/EP2008/008096 (English Translation), report dated Jun. 1, 2010, 8 pages.

*Primary Examiner* — Dawayne A Pinkney
(74) *Attorney, Agent, or Firm* — Skaar Ulbrich Macari, P.A.

(57) ABSTRACT

A spectrometer is described, especially for an optical coherence tomograph for detecting parameters of the human eye, with said spectrometer having an input for measurement radiation to be analyzed, fanning the measurement radiation spectrally out along a direction in a fan and guiding it onto a detector that extends along the direction and comprises a plurality of detector pixels that are sensitive to the measurement radiation, with the spectrometer having an adjusting element which can be adjusted in a controlled manner to adjust the relative position of the fan and the detector, thereby optimizing the incidence position of the fan on the detector, in which it is provided that the detector has at least two superimposed, adjacent pixel lines, and a control device is provided which reads out the superimposed pixels of a plurality of pixel lines in a combined manner for a spectral analysis of the measurement radiation in a pixel binning and evaluates signal differences between superimposed pixels to control the adjusting element and to center the incidence position of the fan at a right angle to the direction of the pixel lines.

20 Claims, 4 Drawing Sheets

U.S. PATENT DOCUMENTS

| | | | |
|---|---|---|---|
| 5,975,699 A | 11/1999 | Hellmuth | |
| 7,480,058 B2 * | 1/2009 | Zhao et al. | 356/497 |
| 2005/0286393 A1 | 12/2005 | Moffat et al. | |
| 2009/0152664 A1 * | 6/2009 | Klem et al. | 257/440 |

FOREIGN PATENT DOCUMENTS

| | | |
|---|---|---|
| WO | WO 2007/030483 | 3/2007 |
| WO | WO 2007/084750 | 7/2007 |
| WO | WO 2009/043517 | 4/2009 |

* cited by examiner

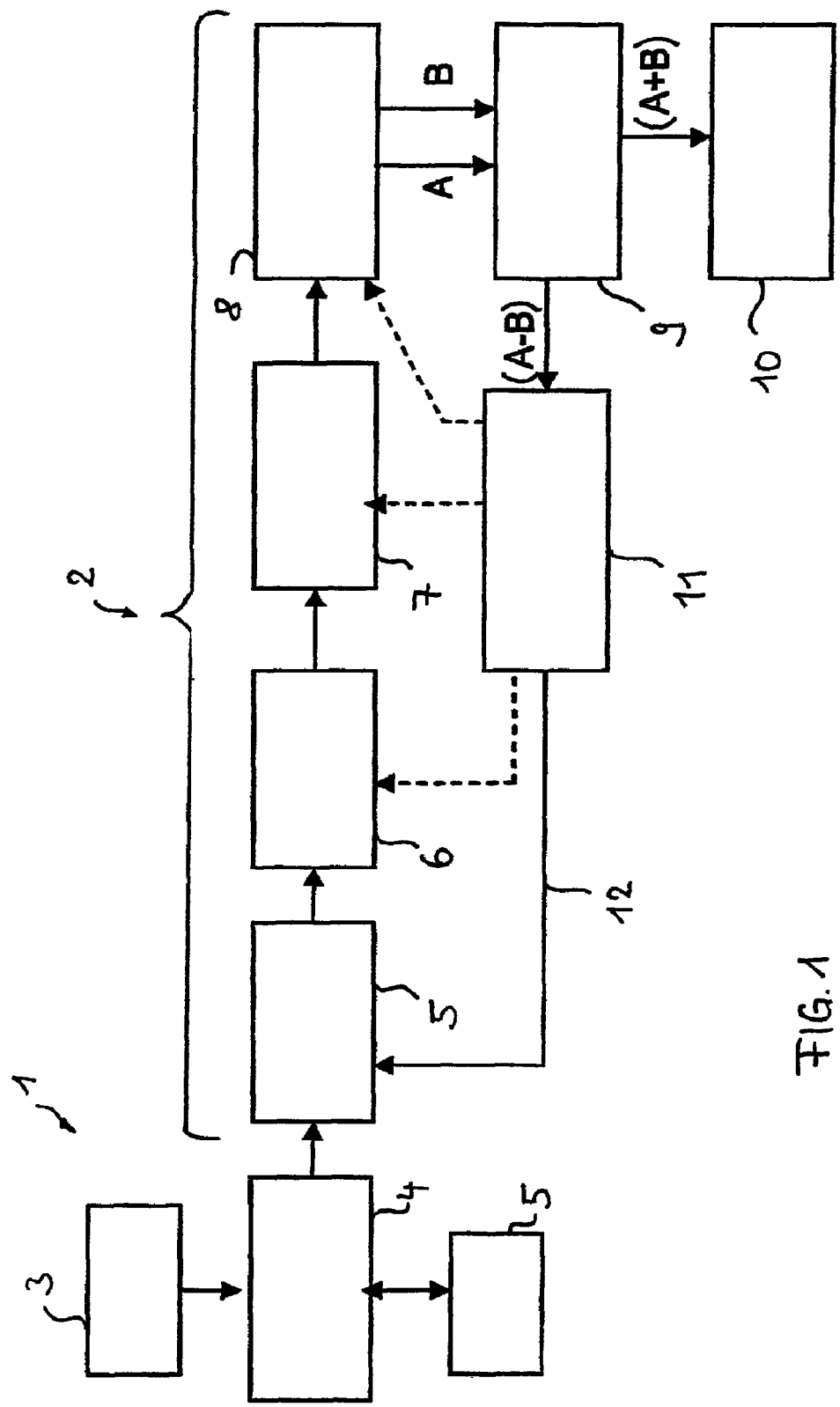

SPECTROMETER

FIELD

The invention relates to a spectrometer, in particular for an optical coherence tomograph for detecting parameters of the human eye, said spectrometer having an input port for measurement radiation to be analyzed, fanning the measurement radiation spectrally out along a direction in a fan and guiding it onto a detector that extends along the direction and comprises a plurality of detector pixels that are sensitive to the measurement radiation, the spectrometer having an adjusting element upstream of the detector which can be controlled to adjust the relative position of the fan and the detector, thereby optimizing the incidence position of the fan on the detector.

The invention further relates to a spectrometer, especially for an optical coherence tomograph for detecting parameters of the human eye, said spectrometer having an input port for measurement radiation to be analyzed, fanning the measurement radiation spectrally out along a direction in a fan and guiding it onto a detector that extends along the direction and comprises a plurality of detector pixels that are sensitive to the measurement radiation.

BACKGROUND

Spectrometers are used widely for analyzing optical radiation. A field that has become especially interesting recently is optical coherence tomography (OCT) in the form of the spectral domain OCT, which is also known as Fourier domain OCT. In this case, the spectrometer spectrally disperses an optical interference signal which originates from the optical coherence tomography and records a spectrum. The OCT image is then obtained by means of a Fourier transformation of the recorded spectrum. The advantage of this OCT technology is the very rapid obtainment of the images and an improved signal-to-noise ratio as compared with other OCT technologies.

The requirements placed on the spectrometer in such application are comparatively high because the spectrometer must show high efficiency in combination with high resolution at the same time. The respectively required precision of mechanics and optics leads to considerable complexity. For example, the detector in the spectrometer needs to be adjusted precisely in the micrometer range. It is not surprising that such spectrometers are very sensitive devices and the long-term stability of the adjustment represents a considerable problem in the construction and production. This problem is exacerbated even further in such a way that such devices need to work in certain applications in a normal clinic or office environment, e.g. during opthalmological examinations, which means they need to be relatively sturdy as compared with other highly precise optical appliances.

The constructional compensation of thermal effects for example in spectrometers for OCT apparatuses requires a high amount of technical complexity in order to ensure the desired positional stability of less than 10 micrometers in beam paths of often more than half a meter in length. This complexity is expressed for example in narrow tolerances for the play of screws and fits, high demands on stability for fixing and gluing the detector, and high demands made on the used materials (specific coefficients of expansion, low ageing or fatigue effects). Moreover, large mechanical pretensions are required for adjustable connections in order to minimize the effects of external mechanical forces which may be the result of transport or a changed installation of the spectrometer.

WO 2007/084750 therefore proposes a spectrometer of the kind mentioned above in which an adjusting element is provided which causes the adjustment of the incidence position of the spectrally fanned radiation to the detector in an actively controlled manner. The spectrometer described in WO 2007/084750 uses one property of the detector line used in the spectrometer there for triggering the adjusting element. In this detector line, one portion of the pixels is offset upwardly over the center of the detector line, and another portion downwardly. By averaging all pixels and comparing the added signal intensity of all upwardly offset pixels with the added signal intensity of all downwardly offset pixels, the spectrometer outlined in the mentioned WO publication generates a triggering signal for the actuating element with the goal of centering the incidence position of the fan on the pixel line transversally to the line direction.

The approach of the WO publication is disadvantageous in the respect that the existence of a group of pixels which is offset upwardly in relation to the center of the pixel line will inevitably lead to the consequence that in the case of a correctly adjusted incidence position of the spectrum on the pixel line either a portion of the pixel surface will not be irradiated (which are the upwardly or downwardly protruding sections of the pixels) or a part of the radiation will not meet the pixels despite correct adjustment and cannot be sensed.

WO 2004/043245 A1 describes a spectrometer for an optical coherence tomograph which comprises a two-dimensional detector which comprises several pixel lines. The pixel lines are illuminated successively by means of a scanning device with spectral radiation in order to have more time for reading out the individual lines. The lines of the two-dimensional detector are therefore used as a kind of image storage means.

SUMMARY

The invention is based on the object of providing a spectrometer of the kind mentioned above in such a way that an adjustment of the incidence position of the spectrally fanned radiation on the detector is possible without encountering the disadvantages as mentioned above. The effort invested in time synchronization between spatial deflection and reading is considerable. High demands are further placed on the imaging optical system because a limitation to the use of a soft central region of the imaging optical system is not possible. That is why the boundary regions of the optical system which are penetrated with radiation during deflection also need to ensure high imaging quality.

This object is achieved in accordance with the invention by a spectrometer, in particular for an optical coherence tomograph for detecting parameters of the human eye, with said spectrometer having an input port for measurement radiation to be analyzed, fanning the measurement radiation spectrally out along a direction in a fan and guiding it onto a detector that extends along the direction and comprises a plurality of detector pixels that are sensitive to the measurement radiation, the spectrometer having an adjusting element upstream of the detector which can be controlled to adjust the relative position of the fan and the detector, thereby optimizing the incidence position of the fan on the detector, and the detector has at least two adjacent pixel lines, which are stacked one on top of each other, and a control device is provided which combines the signals of stacked pixels of a plurality of pixel lines for a spectral analysis of the measurement radiation and which evaluates signal differences between stacked pixels for controlling the adjusting element and for centering the incidence position of the fan perpendicular to the direction of the pixel lines.

This object is further achieved by a spectrometer, especially for an optical coherence tomograph for detecting parameters of the human eye, with said spectrometer having an input port for measurement radiation to be analyzed, fanning the measurement radiation spectrally out along a direction in a fan and guiding it onto a detector that extends along the direction and comprises a plurality of detector pixels that are sensitive to the measurement radiation and is arranged as a two-dimensional planar detector which comprises a plurality of pixel lines which are stacked on top of each other, with a control device being provided which reads out only such pixel lines which are impinged by the fan.

The invention uses a detector with several pixel lines. A pixel line shall be understood to be a plurality of radiation-sensitive elements, so-called pixels, which are lined up along the direction of the detector. The pixel line is illuminated with the spectrally fanned measurement radiation, so that the individual pixels are illuminated with radiation of different intensity, depending on the spectral composition of the measurement radiation. The pixels of the pixel lines are read out individually in order to detect this different radiation intensity and thus the result of the spectral fanning. Furthermore, the radiation intensity fluctuates along the fan depending on spectral composition of the measuring beam.

In a first variant, the invention now uses a detector with at least two stacked or superposed pixel lines which supplies the data required for OCT signal evaluation and, in a special read-out, also supplies sufficient information for determining the relative position of the spectrally fanned radiation in relation to the detector. This information is then used for adjusting the position by means of the adjusting element.

The invention therefore provides two different operating modes of the spectrometer. In a first operating mode, the at least two stacked pixel lines are read out in such a way that the signals of stacked pixels are combined. The combination of adjacent pixels is also known as pixel binning. The pixel binning of superposed pixels, i.e. of pixels which belong to stacked pixel lines, occurs in a measurement operating mode which detects the spectrally fanned radiation. It is obvious that pixels which are disposed along the direction of extension of the detector, i.e. which are arranged along the pixel lines, are read out separately for detecting the spectrum or spectral information. However, this does not exclude that also adjacent pixels are combined into groups of pixels (which are then read out independently) when the pixels are spaced more narrowly in the line than is required for the spectral resolution of the spectrometer. In a second mode, which is an adjusting mode, the signal differences of superposed pixels are evaluated in order to realize the adjustment of the position by means of the adjusting element. This will be explained below.

The (e.g. two) superposed pixel lines guarantee a large effective height of the detector which is available for spectral analysis of the measurement radiation in the measuring mode, e.g. per pixel binning. This simultaneously makes the spectrometer insensitive against mechanical disturbances such as vibrations or changes in position. The active adjustment provided in the adjusting mode reduces the constructional effort which would otherwise be required for compensating thermal effects. The exceptionally low number of lines in comparison with conventional planar 2D-detectors allows a high read-out speed, a good utilization of the detector and thus a high measuring speed at a good signal-to-noise ratio.

The advantage also achieved over planar 2D-sensors without adjustment is that the spectrally fanned measurement radiation will be sensed by always the same pixel lines, which facilitates the inevitable calibration of the sensitivity of the individual pixels (which is also known as pixel response) and the optimization concerning the read-out noise of the detector.

Other than the mentioned WO 2007/084750, the available detector area or incidence area is fully utilized in the case of a correctly adjusted position of the fan in relation to the detector because they are both in perfect overlap. There are no detector areas that would not be illuminated and even none of the areas of the impinging fan would lie off the pixels.

The signal differences between the lines of the multi-line detector are advantageously evaluated in the adjusting mode directly as a feedback signal for determining the relative position between detector and fan and can be used for active adjustment of the position. Such an adjustment can occur intermittently for example or be initiated upon external request, so that the spectrometer is switched at certain times into an adjusting mode in order to center the incidence position of the fan. Such an adjusting mode can be automatically triggered for example on the basis of prior measurement results after a certain period of time after the last adjusting operation lapsed, when the obtained measurement or reference signals fall beneath a threshold value, or upon manual trigger by an operator in the event of maintenance.

The configuration of the spectrometer in accordance with the invention also allows continual adjustment of the position, i.e. a simultaneous operation in measuring and adjusting mode in that the control device subjects the superposed pixels of several pixel lines to an additive and a differential evaluation simultaneously. The control device then uses the summation signal for spectral evaluation of the measurement radiation and the differential signal for adjusting the position. The adjusting can then work under continual feedback control.

Evaluating the differences in intensity for pixels lying on top of each other comes with the advantage that the adjusting mode or adjustment of the position is insensitive to the spectral composition of the radiation to be analyzed. Whereas the signals fluctuate strongly along the direction of the pixel lines since differently intensive spectral lines will usually alternate in the spectrum, the intensity in the fanned beam is substantially constant transversally to the direction of the pixel lines, i.e. for superposed pixels, since radiation of one and the same spectral line will impinge on stacked pixels. The approach pursued here therefore differs significantly from a beam evaluation which would be possible for example for a round beam by using a quadrant detector. Other than is the case in a round beam, the radiation intensity in the fanned measurement beam will fluctuate in an unforeseeable manner in a spectrometer along the pixel line because it depends on the current spectral composition of the measurement radiation.

The multi-line detector can also be provided as a 2D planar detector, i.e. it may have a plurality of pixel lines. The measurement radiation can be analyzed by limiting the read-out of the detector to the pixel lines which are illuminated by the spectrally fanned measurement radiation. As a result of the comparatively large area of the detector, a migration of the incidence position of the fan on the detector is then compensated by the control device in such a way that it chooses other pixel lines of the detector in a matching manner. When 2D planar sensors are used, the width of the fan can be determined for the pixel columns or perpendicular to the direction of the fanning. A minimization of this width can be utilized for signal optimization, e.g. by actively controlling the focusing of the spectrometer, because also the effective spectral resolution (along the sensor) depends on the precise setting of the focusing. The thermal stabilization of the focusing of a spectrometer usually entails considerable constructional effort which can now be reduced due to active compensation.

If one wishes to utilize the advantage in this variant that always the same pixel line is used for detection, or a pixel line from a quantity which is considerably reduced over the entire quantity of pixel lines, the already explained adjustment by means of the adjusting element can also occur in 2D planar detection in that the signal differences are evaluated between pixels of superposed pixel lines. The higher sturdiness concerning changes in the incidence position of the fan on the detector as compared to a variant with a comparatively low number of pixel lines (e.g. two or three pixel lines) will then allow performing adjusting operations to a much rarer extent.

The approach in accordance with the invention is not limited to centering the incidence position of the fan at a right angle to the direction of the pixel lines. It is understood that optionally there can also be an alignment to the center of the pixel lines or a beginning of the pixel lines. There is similarly an optional rotation adjustment of the fan in relation to the detector. In all of these cases it is merely necessary to provide a proper element.

In order to correct a rotational error, the control device evaluates the signal differences between superposed pixels in relation to the position of these pixels along the line. It is thus able to distinguish a displacement perpendicular to the direction of the pixel lines from a rotation. Whereas a displacement changes the signal differences of superposed pixel lines irrespective of the position of the pixels along the pixel line in the same direction in favor of one or the other pixel line, a rotation shows an uneven change, e.g. upwardly disposed pixels are illuminated more strongly in the left region of the pixel lines for example, whereas bottom pixels in the right pixel line region are irradiated more strongly. The control device can thus determine a twisting of the incidence position of the fan in relation to the direction of the pixel lines and can trigger the adjusting device for parallelization of the incidence position of the fan in relation to the direction of the pixel lines.

The use of superposed pixel lines comes with the further advantage that the signals of pixels are compared which register identical spectral components. The problem arises in the mentioned WO 2007/084750 that the pixels compared with respect to their signal differences are disposed entirely besides to one another. Since laterally adjacent pixels can be associated with differently strong spectral lines as a result of the spectral fanning of the measurement radiation, signal differences can arise in laterally adjacent pixels in this case which have nothing to do with the centering of the incidence position of the fan. The WO publication uses an average across a plurality of pixels because of this problem. An average can fail however when a spectrum is present in which there are predominantly intensity maximums on the one pixel group and intensity minimums on the other one. Such a spectrum is obtained for example in a sinus modulation close to the resolution limit. The exclusive use of reference radiation for adjustment as proposed in the WO publication does not reliably remedy the problem because frequently spectral waviness close to or above the resolution limit may occur, e.g. as a result of a Fabry-Perot structure in semiconductors used in the radiation source.

The approach in accordance with the invention does not know these problems because pixels which are substantially or even precisely located on top of each other can always be evaluated concerning the signal differences, which means the compared pixels always reflect the same spectral components. This also applies to a correction in rotation as long as the rotational angle to be corrected lies in a range under 30°, which is always reliably provided in the case of an even only approximate normal pre-adjustment.

Detector elements are possible in the state of the art which have two pixel lines which converge into each other in that the pixels have a triangular basic structure and the pixels of the upper line protrude with the triangular peaks into the cavities of the pixels of the bottom line. Such a detector structure also has several lines within the terms of the present invention as long as two lines are identified whose centers of area of the pixels are spaced transversally to the direction of the lines. Two pixel lines represent such an example where the pixels of the bottom line are arranged in a triangular manner with upwardly facing peaks and the pixels of the upper line are arranged in a triangular manner with downwardly facing peaks which protrude into the cavities left open by the bottom pixel line.

The adjusting element can be a movable mirror. Also, an adaptive mirror can be used or a spatial transmissive light modulator on the basis of liquid crystals with which it is possible to control not only deflection but also focusing, as is described in "Dynamic closed-loop system for focus tracking using a spatial light modulator and a deformable membrane mirror", Optics Express 14, 222-228 (2006), by A. J. Wright, B. A. Patterson, S. P. Poland, J. M. Girkin, G. M. Gibson, M. J. Padgett, or in "Deformable mirror with thermal actuators", Optics Letters 27, 677-679 (2002), by G. Vdovin, M. Loktev.

It is understood that the features or characteristics of individual embodiments as described herein can also be used in combinations other than explicitly mentioned herein, insofar as it is not stated expressly otherwise. Features of described embodiments can also establish an invention individually.

Insofar as individual aspects of a method are described in this description, a respective control device is provided in the apparatus which causes these aspects or steps or acts in that the apparatus is triggered accordingly.

BRIEF DESCRIPTION OF THE FIGURES

The invention is now explained in closer detail by reference to examples shown in the drawings, wherein:

FIG. 1 shows a block diagram of an optical coherence tomograph;

DETAILED DESCRIPTION

Figure 7:
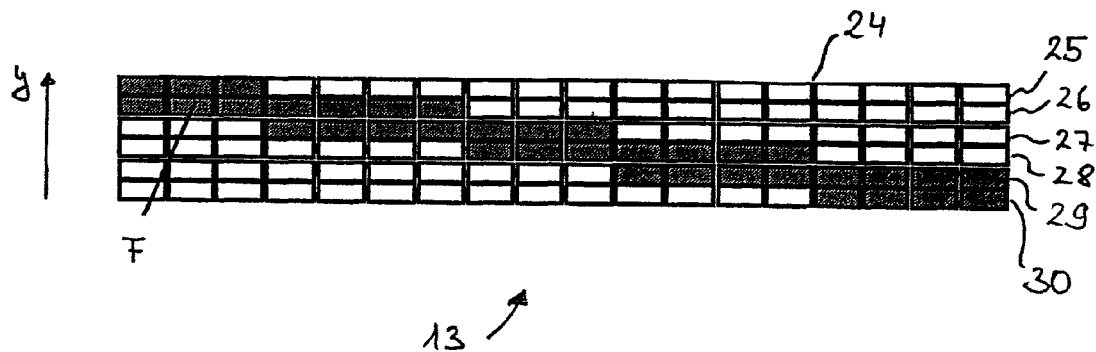
FIG. 7 shows an example for a detector area in a two-dimensionally resolving detector.

FIG. 1 shows a block diagram of an optical coherence tomograph 1 which works according to the Fourier domain method and comprises a spectrometer 2 for this purpose.

The optical coherence tomograph (OCT) 1 comprises a broadband radiation source 3 which feeds an OCT interferometer 4 which interacts with a sample 5, e.g. the human eye. The use in opthalmology is not the only possible application for the OCT 1.

The radiation from the OCT interferometer 4 is analyzed spectrally in the spectrometer 2. The OCT 1 therefore corresponds to a configuration as is known to the person skilled in the art and has been explained for example in WO 2007/084750 or US 2007/0030483 (especially FIG. 11). These specifications are fully incorporated herein by reference insofar as the general OCT configuration is concerned.

Figure 2:
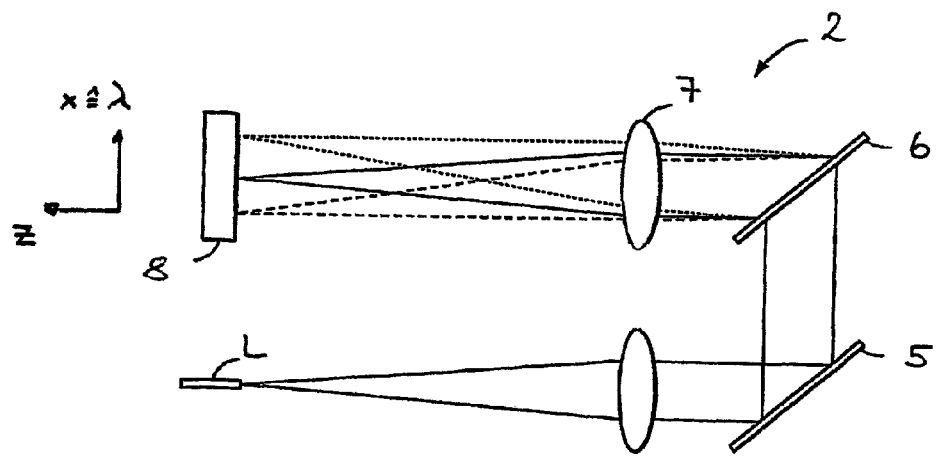
FIG. 2 shows a detailed view of a spectrometer of the optical coherence tomograph of FIG. 1.

FIG. 2 shows a detailed illustration of the spectrometer 2. The radiation originating from the OCT interferometer 4 is supplied via an optical fiber L, the end of which thus represents an input port of the spectrometer 2. The diverging measurement radiation beam emerging from the optical fiber is collimated via focusing optics (not shown in closer detail) and guided to the deflection mirror 5. It guides the beam to a dispersive or diffractive element 6 which is realized in this embodiment as a transmissive grating. It spectrally disperses the radiation and expands it. Imaging optics 7 project the spectral fan to the detector 8.

FIG. 2 shows a system of coordinates for the purpose of better understanding. "z" designates the direction of the optical axis on the detector and "x" the longitudinal direction of the detector 8 along which the radiation is spectrally distributed in a spatial manner. This is symbolized by "x≙λ". The y-axis, which will be explained below, stands perpendicularly to the plane of the drawing of FIG. 2.

Figure 3:
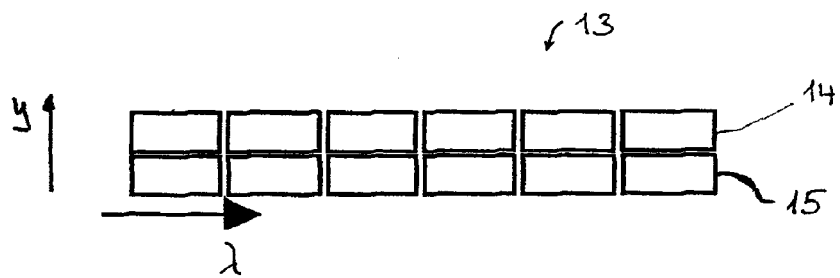
FIG. 3 shows an example for a sensor area of the detector of FIGS. 1 and 2.

Detector area 13 which is sensitive to measurement radiation is shown in FIG. 3 in a top view. It is shown that it consists of two pixel lines 14 and 15 which are arranged above one another in the y-direction which lies perpendicular to the spreading direction of the spectral fan (as will be explained below). The detector 8 resolves the radiation according to its wavelength λ along the pixel lines 14, 15 which is why the longitudinal coordinates of the pixel lines are also associated with λ values. It is obvious that the FIG. 3 and the following drawings merely show a section of a detector which is much longer, or a fan which is much longer in the λ direction.

Figure 4:
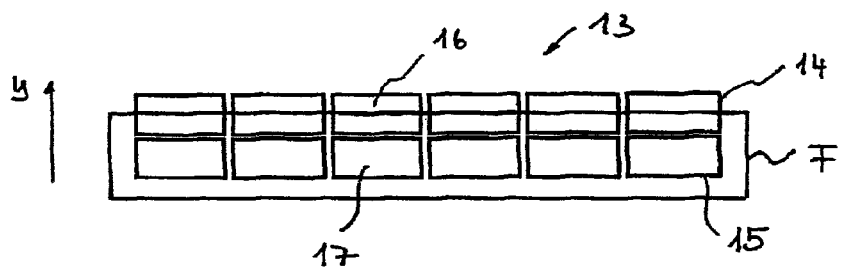
FIG. 4 shows an illustration similar to FIG. 3 with an entered incidence area of a spectrally fanned measurement radiation.

FIG. 4 shows how the incidence position F of the fan of the spectrally fanned radiation lies in relation to the detector area 13 of the detector 8 in case of a misalignment. The incidence position F is displaced downwardly along the y-direction in relation to the detector area 13.

The misalignment leads to the consequence that the signal strength of a pixel 16 located in the upper pixel line 14 differs from the signal strength of the pixel 17 of the other detector line 15 which is beneath the same. Pixel 17 is irradiated fully, but the pixel 16 only approximately half as much. This signal difference is now used by the control device 9 in that the signal difference is determined. This is shown schematically in FIG. 1 in such a way that the control device 9 reads out the signals (A+B) of the pixel lines 13 and 14 at first in a separate manner and then feeds the signal difference (A−B) to a controller 11 which is part of the control unit and controls the deflection mirror 5 via a control line 12.

As will be explained below in closer detail, this causes a displacement of the incidence position F of the fan in relation to the detector area 13. The incidence position F of the fan is centered in the y-direction on the detector area 13 by minimizing the signal differences between the pixels 16 and 17 (which are obviously only used as examples for superposed pairs of pixels) during the progress of the feedback control. The summation value (A+B) of the signals will thus rise, which the control device 9 provides to an evaluation unit 10 which is also a component of the control unit and evaluates the spectrally resolved measurement radiation of the OCT interferometer 4 for obtaining an image, e.g. for a conventional A scan.

Figure 5:
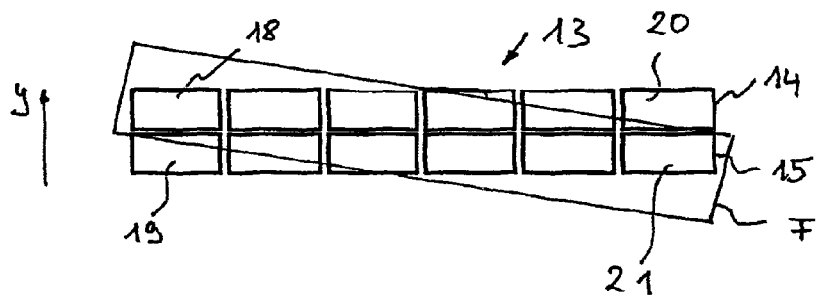
FIG. 5 shows an illustration similar to the one of FIG. 4, with the incidence area not being axially displaced but twisted.

FIG. 5 shows a case in which the incidence area F is twisted in relation to the detector area. This leads to the consequence that pixels disposed to the left and right of the center of the pixel lines 14 and 15 will show a signal difference with a different algebraic sign. The pixel 18 at the left edge is irradiated fully, whereas the pixel 19 is irradiated only to a minor extent. At the right edge however the pixel 21 of the bottom pixel line 15 is fully irradiated and the pixel 20 of the upper pixel line 14 supplies virtually no signal at all. The control device 9 and the controller 11 recognize a rotational misalignment from the fact that the differential signal (A−B) changes its algebraic sign via the λ direction of the pixel lines 14, 15. It then controls the deflection mirror 5 in a respective manner.

It is obvious that another element which influences the relative position of incidence position F and detector area 13 can be used instead of the deflection mirror. Actions on the dispersive element 6, the imaging optics 7 or the detector 8 which can be moved in a suitable manner for example are possible in this case. Such actions are shown in a broken line in FIG. 1. The action can also occur on an element that represents a combination of dispersive element 6 and imaging optics 7 such as an imaging grating for example.

Figure 6:
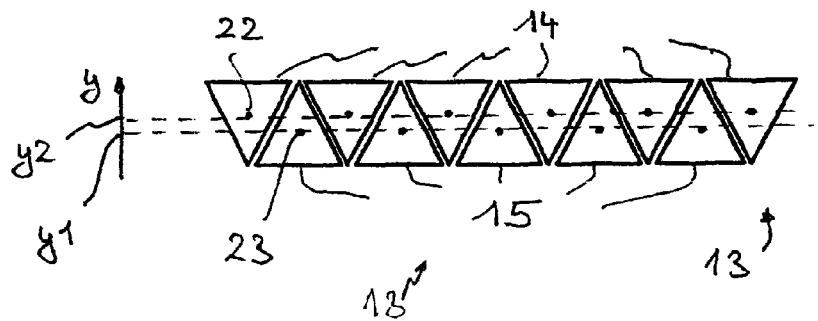
FIG. 6 shows a further example for the detector area of the detectors of FIGS. 1 and 2.

FIG. 6 shows a further embodiment for the detector 8 which in the underlying configuration also consists of two pixel lines. The detector area 13 is formed here by triangular pixels. Pixels with upwardly facing peaks alternate with pixels with downwardly facing peaks. The pixels with downwardly facing triangular peaks are disposed with respect to their center of area 22 above the pixels with the upwardly facing peaks whose center of area 23 is disposed lower in the y-direction. As a result, the upper pixel line 14 is formed by the pixels whose center of area 22 is arranged at a higher y-value and the bottom pixel line 15 by the pixels whose center of area 23 is disposed comparatively lower.

FIG. 7 finally shows the detector area 13 of a two-dimensionally resolving detector 24 with considerably more than two pixel lines (merely six lines 25 to 30 are shown in the drawing for reasons of simplicity). The planar detector thus provided allows a rapid and, at the same time, low-noise read-out of the spectrally fanned measurement radiation by choosing the pixels which are covered by the incidence area F of the fan (shown in grey).

In one embodiment, the adjustment of the incidence area F in relation to the detector area 13 as explained by reference to FIGS. 4 to 6 is also performed in the detector configuration according to FIG. 7.

Figure 8:
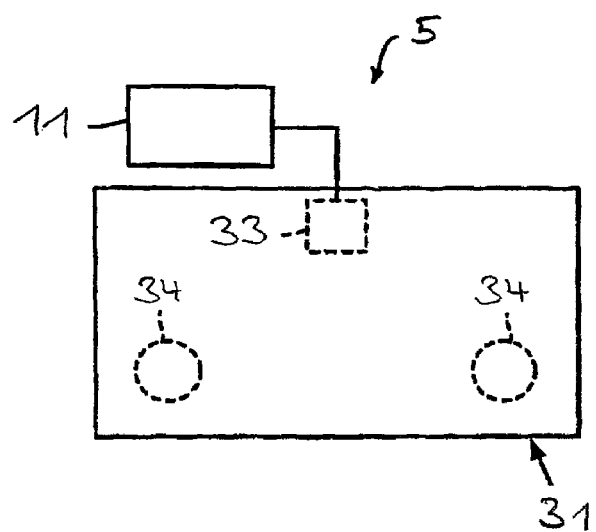
FIGS. 8 and 9 show an embodiment for an adjusting element used in the spectrometer.
Figure 9:
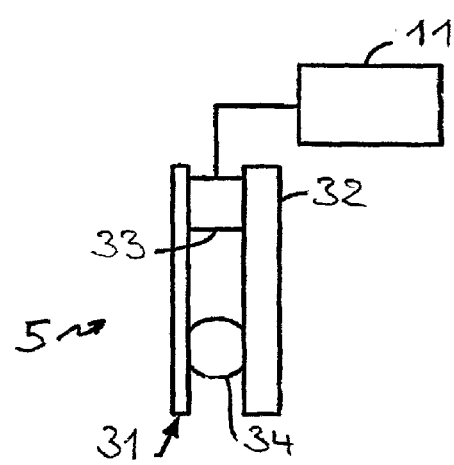

FIGS. 8 and 9 show an example for the controlable deflection mirror 5, with FIG. 8 showing a top view and FIG. 9 a side view.

The deflection mirror 5 comprises a mirror face 31. Said mirror face 31 is fastened to a base part 32 wherein a piezo-actuator 33 connects the mirror 31 with the base part 32.

The mirror 31 is further held via support balls 34 on the base part 32. Electric control of the piezo-actuator 33 thus causes a tilting of the mirror face 31 and thus a setting of the adjusting element. The piezo-actuator 33 is suitably connected for this purpose with the controller 11.

A modification two double-axis tilting is also a possible option.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A spectrometer for detecting parameters of the human eye, comprising:
    a detector extending along a detection direction, the detector including a plurality of detector pixels that are sensitive to a measurement radiation, the detector also including at least two adjacent pixel lines that are stacked on top of each other;
    an input port for receiving the measurement radiation to be analyzed, the input port configured to fan the measurement radiation spectrally out along a first direction and guide the fanned measurement radiation onto the detector;
    an adjusting element configured to controllably adjust the relative position of the fanned measurement radiation and the detector;
    a control device which evaluates signal differences between two or more pixels in the stacked pixel lines, controls the adjusting element, and centers the incidence position of the fanned measurement radiation perpendicular to the detection direction of the at least two adjacent pixel lines.

2. The spectrometer according to claim 1, wherein the control device is further configured to cause the evaluation of the signal differences and the centering of the incidence position of the fanned measurement radiation in an adjusting operation of the spectrometer to be performed only intermittently.

3. The spectrometer according to claim 1, wherein the control device is further configured to cause the evaluation of the signal differences and the centering of the incidence position of the fanned measurement radiation in an adjusting operation of the spectrometer to be performed only upon external demand.

4. The spectrometer according to claim 1, wherein the control device is configured to subject a superposed pixel of the plurality of pixel lines to a summary and a differential evaluation, wherein a summation signal is used for spectral analysis of the measurement radiation, and a differential signal is used for triggering the adjusting element and for centering the incidence position of the fanned measurement radiation.

5. The spectrometer according to claim 1, wherein the adjusting element is configured to rotate the fanned measurement radiation in relation to the detection direction.

6. The Spectrometer according to claim 1, wherein the control device is configured to evaluate signal differences between a superposed pixel in relation to a position of the superimposed pixel along the pixel lines in order to determine a twisting of the incidence position of the fanned measurement radiation in relation to the direction of the pixel lines.

7. The Spectrometer according to claim 1, wherein the control device is configured to control the adjusting element for parallelizing the incidence position of the fanned measurement radiation in relation to the direction of the pixel lines.

8. An optical coherence tomograph for detecting parameters of the human eye, the tomograph comprising:
    a detector comprising a two-dimensional planar element having a plurality of detector pixels and a plurality of superposed pixel lines that are sensitive to a measurement radiation;
    an input port configured to analyze measurement radiation, fan the measurement radiation spectrally out along a detection direction and guiding the fanned measurement radiation onto the detector; and
    a control device configured to read out only pixel lines of the detector on which the fanned measurement radiation impinges.

9. The tomograph according to claim 8, further comprising:
    an adjusting element configured to adjust the relative position of the measurement radiation and the detector, thereby optimizing an incidence position of the fanned measurement radiation on the detector.

10. The tomograph according to claim 9, wherein the control device is configured to evaluate a signal difference between the superimposed pixels for centering the incidence position of the fanned measurement radiation perpendicular to the direction of the pixel lines.

11. The tomograph according to claim 9, wherein the adjusting element is configured to rotate the fanned measurement radiation in relation to the detection direction.

12. The tomograph according to claim 9, wherein the control device is configured to control the adjusting element for parallelizing the incidence position of the fanned measurement radiation in relation to the direction of the pixel lines.

13. The tomograph according to claim 8, wherein the control device is configured to evaluate signal differences between superposed pixels in relation to a position of the superimposed pixels along the pixel lines in order to determine a twisting of an incidence position of the fanned measurement radiation in relation to the direction of the pixel lines.

14. A method for detecting parameters of the human eye, the method comprising:
    receiving a measurement radiation to be analyzed;
    fanning the measurement radiation spectrally out along a first direction;
    guiding the fanned measurement radiation onto the detector;
    adjusting the relative position of the fanned measurement radiation and the detector to optimize an incidence position of the fanned measurement radiation on the detector;
    reading out superposed pixels for a plurality of pixel lines for a spectral analysis of the measurement radiation
    evaluating a signal difference between superposed pixels, centering the incidence position of the fanned measurement radiation perpendicular to the direction of the at least two adjacent pixel lines.

15. The method of claim 14, wherein the steps of evaluating a signal difference between superposed pixels and centering the incidence position of the fanned measurement radiation perpendicular to the direction of the at least two adjacent pixel lines is performed only intermittently.

16. The method of claim 14, wherein the steps of evaluating a signal difference between superposed pixels and centering the incidence position of the fanned measurement radiation perpendicular to the direction of the at least two adjacent pixel lines is performed only upon external demand.

17. The method of claim 14, further comprising subjecting the superposed pixels of the plurality of pixel lines to a summary and a differential evaluation, wherein a summation signal is used for spectral analysis of the measurement radiation, and a differential signal is used for triggering the adjusting element and for centering the incidence position of the fanned measurement radiation.

18. The method according to claim 14, further comprising rotating the fanned measurement radiation in relation to the detector.

19. The method according to claim 14, further comprising evaluating signal differences between superposed pixels in relation to a position of the superimposed pixels along the pixel lines in order to determine a twisting of the incidence position of the fanned measurement radiation in relation to the direction of the pixel lines.

20. The method according to claim 14, further comprising parallelizing the incidence position of the fanned measurement radiation in relation to the direction of the pixel lines.

\* \* \* \* \*